United States Patent [19]

Kehrbach et al.

[11] Patent Number: 4,554,274

[45] Date of Patent: Nov. 19, 1985

[54] $N_b$ QUATERNARY DERIVATIVES OF AJMALINE AND ISOAJMALINE, METHODS AND INTERMEDIATE PRODUCTS IN THE MANUFACTURE OF THEIR DERIVATIVES AND METHOD OF USING SAME AND PHARMACEUTICAL COMPOSITIONS THEREOF

[75] Inventors: Wolfgang Kehrbach, Hanover; Joachim Wegener, Algermissen; Ulrich Kuehl, Hanover; Renke Budden, Hanover; Gerd Buschmann, Hanover, all of Fed. Rep. of Germany

[73] Assignee: Kali-Chemie Pharma GmbH, Hanover, Fed. Rep. of Germany

[21] Appl. No.: 615,757

[22] Filed: May 31, 1984

Related U.S. Application Data

[63] Continuation of Ser. No. 391,822, Jun. 24, 1982, abandoned, which is a continuation of Ser. No. 195,487, Oct. 9, 1980, abandoned.

[30] Foreign Application Priority Data

Oct. 13, 1979 [DE] Fed. Rep. of Germany ....... 2941529

[51] Int. Cl.[4] ................. A61K 31/435; C07D 455/00; C07D 471/08
[52] U.S. Cl. .................................. 514/239; 514/279; 514/281; 544/125; 546/40; 546/43
[58] Field of Search .................. 546/40, 43; 544/125; 424/248.57, 256; 514/239, 279, 281

[56] References Cited

PUBLICATIONS

Petter et al., "The Antifibrillatory Effect on the Heart of Ajmaline, Bromo-Ajmaline, Quinidine and Novocainamide", (1962).

*Primary Examiner*—Donald G. Daus
*Assistant Examiner*—Diana G. Rivers
*Attorney, Agent, or Firm*—Schwartz, Jeffery, Schwaab, Mack, Blumenthal & Evans

[57] ABSTRACT

New quaternary derivatives of 10-bromoajmaline and 10-bromoisoajmaline are disclosed which exhibit antiarrhythmic and adrenolytic properties and which have the formula I

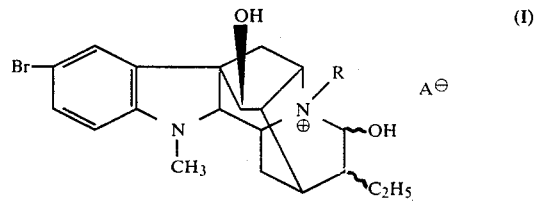

wherein R represents a carbon-attached organic group containing 1 to 10 carbon atoms and $A^-$ represents an acid anion as well as pharmaceutical formulations thereof and processes and intermediates for their preparation.

8 Claims, 2 Drawing Figures

N$_b$ QUATERNARY DERIVATIVES OF AJMALINE AND ISOAJMALINE, METHODS AND INTERMEDIATE PRODUCTS IN THE MANUFACTURE OF THEIR DERIVATIVES AND METHOD OF USING SAME AND PHARMACEUTICAL COMPOSITIONS THEREOF

BACKGROUND OF THE INVENTION

This is a continuation of application Ser. No. 391,822, filed June 24, 1982, which is a continuation of Ser. No. 195,487 filed Oct. 9, 1980, both now abandoned.

The invention relates to new 10-brominated N$_b$-quaternary derivatives of ajmaline and isoajmaline, processes and intermediate materials for their preparation and pharmaceutical compositions and methods of treatment using same.

Ajmaline is an indole alkaloid from the group of rauwolfia alkaloids. Quaternary salts of ajmaline are known to possess valuable pharmacological properties, in particular, antiarrhythmic properties.

From German Pat. Nos. 11 54 120, 11 96 207 and 16 20 559, N$_b$-quaternary derivatives of ajmaline and isoajmaline are known which exhibit valuable pharmacological activities in particular antiarrhythmic activity. A well known representative of these known quaternary ajmaline derivatives is N$_b$-propyl ajmalinium hydrogen tartrate which is the active ingredient of an antiarrhythmic pharmaceutical composition which is commercially available under the trademark Neo Gilurytmal ®, and is used in the treatment of disorders of the coronary and circulatory system.

It is well known that quaternary ajmaline derivatives in addition to their desirable pharmacological properties also possess some undesirable side effects, e.g. negative inotropic properties.

SUMMARY OF THE INVENTION

It is an object of the present invention to provide new pharmacologically active ajmaline derivatives which exhibit improved pharmacological properties and in particular possess strong cardiac rhythm regulative properties and an increased physiological compatability.

It is a further object of the present invention to provide new antiarrhythmic compounds which are low in side effects, especially low in negative inotropic side effects and low in toxicity.

It is a further object of the present invention to provide new ajmaline derivatives which exhibit adrenolytic properties.

It is a further object of the present invention to provide processes for the preparation of such quaternary ajmaline derivatives.

It is still a further object of the present invention to provide pharmaceutical solid or liquid formulations containing such quaternary ajmaline derivatives.

It is a further object of the present invention to provide a method of treatment or prevention of diseases of the coronary and circulatory system, especially heart rhythm disorders.

In order to accomplish the foregoing objects according to the present invention there are provided novel N$_b$-quaternary 10-bromoajmaline and 10-bromoisoajmaline compounds of the formula I wherein R is a carbon-attached organic residue containing 1 to 10 carbon atoms which may further contain at least one halogen atom or at least one oxygen atom or at least one nitrogen atom or at least one oxygen and one nitrogen atom; and A$^\ominus$ is an anion of an organic or inorganic acid.

According to the present invention, there are further provided processes for preparing the compounds of formula (I) and of the intermediate aldehydes of formula IV The new compounds of formula I exhibit valuable pharmacological properties, especially antiarrhythmic and adrenolytic properties.

According to the present invention there are further provided pharmaceutical compositions comprising the above-described compounds of formula I and inert diluents.

Further objects, features and advantages of the present invention will become apparent from the detailed description of the invention and the figures of drawings below.

DETAILED DESCRIPTION OF THE INVENTION

Within the formula (I) R may represent a group containing 1 to 10 carbon atoms and having the formula II wherein n is 0 or 1; m is 0 or 1; x is hydrogen, hydroxy, straight or branched alkyl which is unsubstituted or is substituted, phenyl which is unsubstituted or is substituted, dialkylamino, pyrrolidino, piperidino or morpholino; and y is hydrogen, hydroxy or methyl or x and y together form a bond with the proviso that when y is hydroxy n is 1 and that when x and y together form a bond n and m each are 1.

When x represents alkyl, this alkyl group may be unsubstituted or substituted by hydroxy, alkoxy, halogen or dialkylamino.

When x represents phenyl, this phenyl group may be unsubstituted or substituted by alkyl, alkoxy or halogen.

Most preferably R represents one of the following: methyl, ethyl, allyl, propyl, butyl, 3-methylbutyl, hexyl, decyl, benzyl, 4-fluorobenzyl, 4-methoxybenzyl, 2-hydroxyethyl, 2-hydroxy-2-phenylethyl, 2-diethylaminoethyl, 3-diethylaminopropyl, 2-(1-pyrrolidinyl)ethyl, 2-(1-piperidinyl)ethyl, 2-(4-morpholinyl)ethyl or 2-hydroxy-3-(1-piperidinyl)propyl.

Advantageously, $A^\oplus$ represents the anion of a pharmacologically acceptable acid, preferably an anion of tartaric acid, oxalic acid, citric acid, hydrochloric acid or phosphoric acid, most preferably an anion of tartaric acid.

The 10-brominated $N_b$-quaternary ajmaline and isoajmaline compounds can be prepared in the following manner.

Compounds of formula III that is 10-bromoajmaline of formula IIIa wherein 21-hydroxy substituent is in alpha-position and the 20-ethyl substituent is in the beta-position or 10-bromoisoajmaline of formula IIIb wherein the 21-hydroxy substituent is in the beta-position and the 20-ethyl substituent is in the alpha-position are alkylated with an alkylating agent of the formula R—Z wherein R is as defined above and Z is halogen or an acid residue of a reactive ester, to obtain compounds of formula Ia wherein R and Z are as defined above.

The alkylating agent preferably is a compound of formula V wherein n, m, x and y are as defined above and Z represents chlorine, bromine, iodine or tosyl. Thus within the process according to the present invention alkylating agents not only include alkyl halides but also the halides and tosylates of optionally substituted alkyl and phenylalkyl groups, as is further demonstrated by the examples below.

The quaternization of the compounds of formula (III) can be performed in any conventional manner. Equimolar amounts of the starting materials may be used. Advantageously, an excess of the alkyl halide may be used. It is advisable to effect the quaternizing reaction in the presence of an organic solvent which is inert towards the reacting compounds. Suitable solvents are, for example, acetonitrile, chloroform, dimethylformamide, sulfolane (also known as 2,3,4,5-tetrahydrothiophen-1,1-dioxide), dioxane or lower alkyl alcohols, such as for example, methanol and ethanol. Alkylating agents which under the reaction conditions do not react with themselves may also serve as a solvent. The reaction is suitably carried out at elevated temperature preferably at reflux temperature of the solvent. Yet, in particular, where the solvent has a high boiling point, the reaction may also be carried out at temperatures below the reflux temperature.

The quaternary salts of 10-bromoajmaline and 10-bromoisoajmaline which are obtained from the above alkylation may themselves be final products where the anion of the salt is a pharmacologically acceptable anion and quaternary is suitable for the intended galenic formulation.

If a quaternary salt is not suitable for the intended use, e.g. because it is hygrosopic or the anion therein is not pharmacologically acceptable, the quaternary salt of formula I can be transformed into the corresponding open-ring aldehyde base of formula IV wherein R is as defined above by treatment with an alkaline agent. The latter can be subsequently reacted with an acid of the formula $H^\oplus A^\ominus$ wherein $A^\oplus$ is as defined above to form any quaternary salt of formula I.

Suitable alkaline agents for transforming a quaternary salt of formula I into the corresponding aldehyde base include aqueous solutions of alkaline compounds. Particularly suitable alkaline solutions are alkali hydroxide solutions, especially a 10% sodium hydroxide solution, or a solution of sodium hydrogen carbonate or sodium carbonate. It is advisable to effect the reaction in the presence of a suitable extracting solvent. All inert solvents which are not water-miscible are appropriate such as chloroform, methylene chloride, ethyl acetate, diethylether, and the like, wherein the aldehyde bases are sufficiently soluble.

After distilling off the extracting solvent, advantageously under vacuum, the basic aldehyde bases are recovered in amorphous form.

Finally, the thus prepared aldehyde bases can be reacted with a pharmacologically acceptable acid, e.g., one of the above cited organic or inorganic acids to form the quaternary salt of formula I. It is not necessary that the aldehyde base is isolated prior to treating it with the acid. The raw dried and clarified organic extract obtained from the alkaline treatment of the quaternary salt of formula Ia can be used as such.

Aldehyde bases of formula IVa wherein R' is a group of the formula IIa wherein m and x are as defined above may also be obtained directly by alkylating a compound of formula III with an epoxide of formula VI wherein m and x are as defined above. The aldehyde base can then be treated with an acid $H^\oplus A^\ominus$ to obtain the corresponding quaternary salt of formula I.

Since the ring-open aldehyde base are amorphous not crystalline, they do not exhibit a definite melting point. Optical rotation values also cannot be used for exact characterization of the compounds, since during the quaternization of bromoajmaline or bromoisoajmaline respectively an isomerization at the carbon atoms in 20- and 21-position may take place. Independently of whether the starting material is pure bromoajmaline or pure bromoisoajmaline, this isomerization leads to a mixture of the stereoisomer quaternary salts or aldehyde base yet the composition of the mixture varies depending on whether the starting material is bromoajmaline or bromoisoajmaline. The degree of isomerization is dependent on the special requirement of the group R and the type of its substitution.

The ratio between the isomers may also vary from one experiment to another in case the reaction conditions are not exactly the same. During the transformation of the aldehyde base into the quaternary salt the ratio between the isomers can be changed further.

Therefore the ring-open aldehyde bases are most advantageously characterized by the position of the resonance of the aldehyde proton in the $^1$H-NMR-spectrum and by the occurrence of a carbonyl-band in the infrared-spectrum. The resonance occurs at 9.0–9.6 δ whereas the carbonyl band appears at about 1700–1720 $cm^{-1}$.

Figure 1:
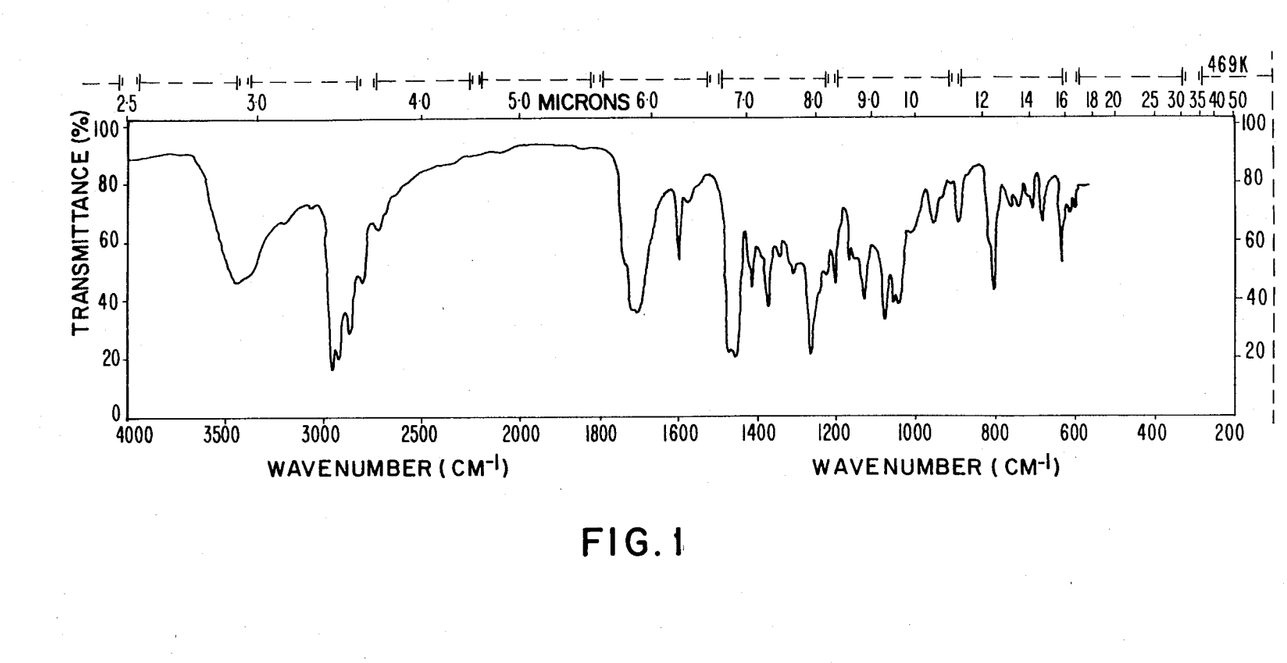
FIG. 1 represents the infrared-spectrum of the aldehyde base derived from N$_b$-propyl-10-bromoiosajmaline.
Figure 2:
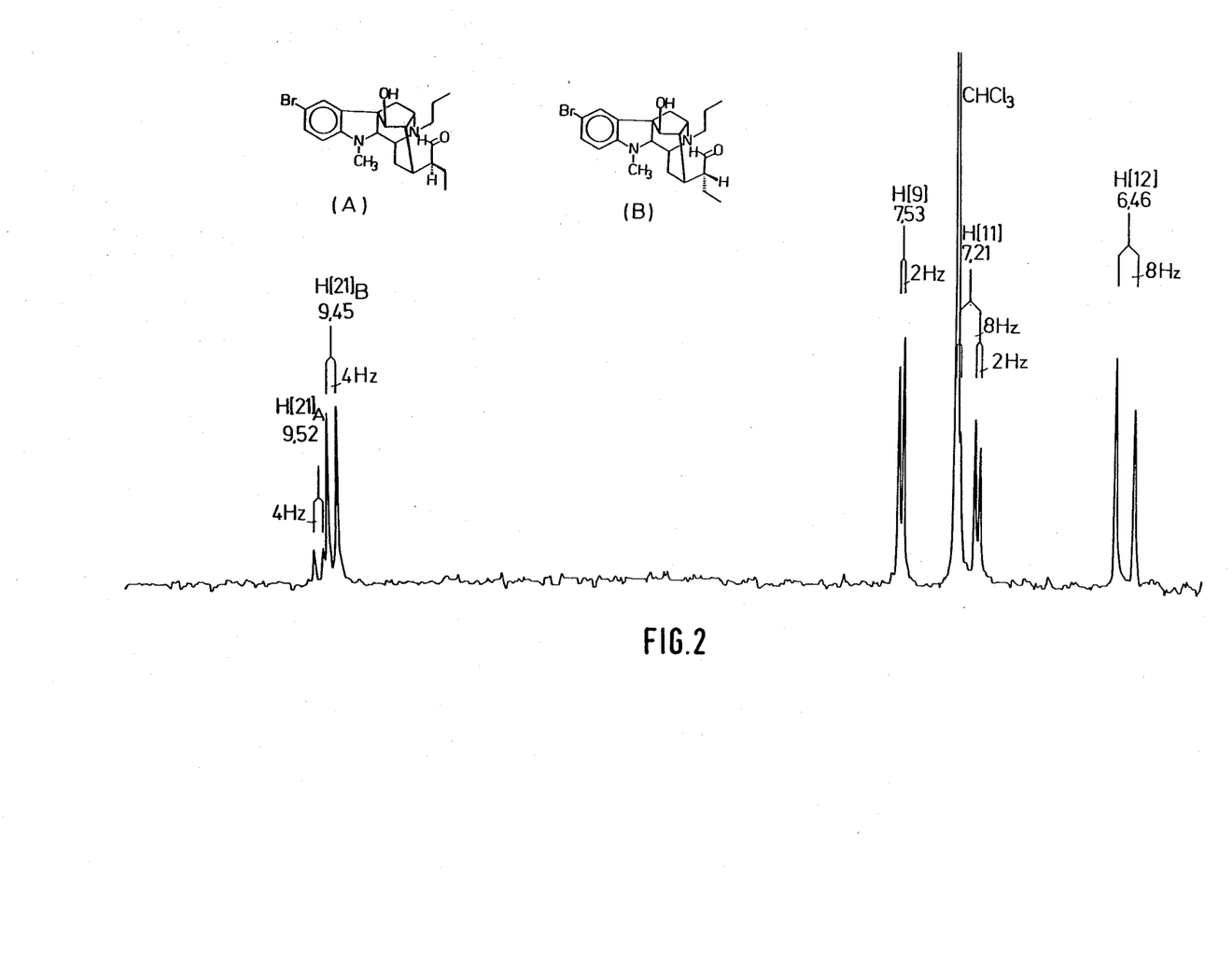
FIG. 2 represents a portion of the 90 MHz $^1$H-FT-NMR-spectrum of the same compound.

FIGS. 1 and 2 show the infrared spectrum and a portion of the 90 MHz $^1$H-FT-NMR-spectrum respectively of a representative aldehyde base, namely the aldehyde base derived from $N_b$-propyl-10-bromoisoajmaline. In the infrared spectrum the C=O band is seen at 1710 $cm^{-1}$. In the NMR-spectrum the resonance of the O=CH aldehyde proton at C21 which appears in the low field is characteristic. It is split with a frequency of 4 Hz by coupling with only adjacent proton at C20. The occurrence of two signals is due to the presence of a mixture of two isomer forms, the n-form (signal at 9.52) and the iso-form (signal at 9.45). The ratio between the isomers can be estimated from the respective heights of the peaks. The isolated aldehyde base, after isolation or in form of a solution in the extracting solvent is subsequently reacted with a pharmacologically acceptable organic acid preferably tartaric acid, oxalic acid, citric acid, hydrochloric acid or phosphoric acid and thereby is converted into the quaternary compound.

Where in the following the terms "n-form" or "iso-form" are used these terms pertain exclusively only to the configuration at the C20-position. The 21-hydroxy substituent usually is in trans-position yet can also be in cis-position.

The $N_b$-quaternary compounds of formula (I), according to the present invention, exhibit valuable pharmacological properties and therefore are useful in medical treatment. In particular, they are useful in the treatment and prophylaxis of diseases of the coronary and circulatory system, e.g., they are useful as antiarrhythmics in the treatment of heart rhythm disorders, since they exhibit adrenolytic and antiarrhythmic activities, as is indicated in standard tests, e.g., measurement of the functional refractory period and the contraction force in the isolated left atria of a guinea pig.

For the above-mentioned uses, the administered doses can vary considerably depending on the type of the compound, the animal, the mode of administration, the treated conditions and the therapy which is desired. Usually satisfactory results are obtained with dosages between 0.05 and 25 mg/kg body weight. These doses can be administered enterally, preferably orally, or parenterally. For example, daily oral doses for larger mammals can be chosen between 0.5 and 100 mg.

Surprisingly, the new compounds of formula (I) are considerably more active, and physiologically better acceptable than the known ajmaline derivatives. Thus, in comparison with known ajmaline derivatives, the effect of the new compounds is similar to that of the ajmaline derivatives at considerably lower dosages. Furthermore, the undesirable negative inotropic effect, which is observed with the ajmaline compounds, is reduced, and at the same time the new compounds of formula (I) exhibit an increased therapeutic range.

According to a further feature of the invention there are provided pharmaceutical compositions containing at least one of the compounds of formula (I). The compounds of formula (I) are stable and storable in aqueous solution, as well as in the solid state. The compositions may take the form of solid or liquid formulations for enteral, preferably oral, or for parenteral administration. Thus, the formulations may be in the form of capsules, tablets, coated tablets, suppositories, emulsions or solutions. These formulations may comprise conventional pharmaceutical carriers, e.g. solids, such as starch, lactose, mannit, polyvinyl pyrrolidone or liquids such as sterile water, pharmaceutically acceptable alcohols or fatty oils, and may further comprise pharmaceutical adjuvants, e.g., binders or lubricants for tabletting, stabilizing, flavoring or emulsifying agents.

The superior properties of the compounds according to the present invention is seen from the pharmacological data given in the table below wherein the pharmacological properties of representatives of the compounds of the present invention are compared with those of the known $N_b$-propylajamlinium hydrogen tartrate (trademark Neo Giluritmal ®). The following data are given in the table:

The acute toxicity of the compounds is determined in male NMRI-mice (body weight range 18–22 g) after oral (p.o.) and intraperitonal (i.p.) administration. The $LD_{50}$ is defined as that dose in μmol/kg which causes a 50% mortality rate of the test animals on the 7th day after application. The calculation of the $LD_{50}$ is carried out by probitanalysis (see L. Cavalli-Sforza, Grundbegriffe der Biometric, Gustav Fischer Verlag Stuttgart (1964)).

The minimum symptom dose is determined in male NMRI-mice (body weight range 18–22 g) according to the procedure of Campbell and Richter (see D. E. S. Campbell and W. Richter, Acta Pharmacol. Toxicol. 25 (1967), pp. 345–363). The minimum symptom dose is defined as that dose in μmol/kg which after i.p. administration causes changes in behavior in 2 out of 3 mice.

The minimum symptom dose is a measure for evaluations undesirable side effects.

The prolongation of the functional refractory period (FRP) and the contraction force (CF) in the isolated left atria of female guinea pigs (albinopirbright-white guinea pigs, body weight range 300–400 g) are determined according to the double stimulus method of Govier (see W. C. Govier, J. Pharmakol, Exp. Ther. 148 (1965) pp. 100–105). The concentrations which are given in the table below are the concentrations in 82mol/l which 18 minutes after application leads to a prolongation of the functional refractory period to 125% or respectively to a reduction of the contraction force to 75% of the starting value. Furthermore the ratio between contraction force-reducing dose and functional refractory period-prolonging dose is given. This ratio is an indication of the therapeutic range of the antiarrhythmic effect on the isolated organ (see K. Greef, Verh. Dtsch. Ges. Kreislaufforsch. 35 (1969) pp. 88–97).

To determine the influence of the active ingredient on male Wista rats (weighing 280 to 350 g), infusion with aconitine according to the method of Raschak is carried out (M. Raschak, Arzneim. Forschung (Drug Research) 25 (4) (1975) pp. 639–641). The results are given as the difference (that is, the difference in time as Δ%) between the active substance and a control sample in bringing about a disruption of heart rhythms (extrasystolic (ES), ventricular tachicardiea (VT), chamber flutter (KF)). In the control sample the active ingredient is replaced by a vehicle such as isotonic NaCl-solution or solution medium. The administration of the active ingredient is in a dosage of 1/20th of the $LD_{50}$ and a constant concurrent infusion per unit of time of aconitine.

Since some of the data are given in μmol/kg and μmol/l respectively, the calculated molecular weight (MW) of the test compounds is also given in the table below.

TABLE

| Example | Active Ingredient R | NW | $LD_{50}$ i.p. μmol/kg | $LD_{50}$ p.o. μmol/kg | Min. Symptom-dose μmol/kg | Isolated Guinea Pig Atria CF μmol/l | Isolated Guinea Pig Atria FRP μmol/l | CF/FRP | Aconitin-Rat ES Δ% | Aconitin-Rat VT Δ% | Aconitin-Rat KF Δ% |
|---|---|---|---|---|---|---|---|---|---|---|---|
| Comparison (Neo-Giluryt mal) | n-C$_3$H$_7$ | 519 | 41 | 65 | 12 | 0.26 | 1.8 | 0.15 | +86 | +80 | +50 |
| (11.b) | —CH$_3$ | 569 | 190 | 1289 | 88 | 9.0 | 7.2 | 1.3 | +85 | +73 | +52 |
| (12.b) | —C$_2$H$_5$ | 583 | 122 | 1430 | 21 | 1.4 | 1.5 | 0.9 | +52 | +55 | +39 |
| (13.b) | n-C$_3$H$_7$ | 598 | 118 | 437 | 42 | 1.5 | 0.6 | 2.4 | +110 | +130 | +110 |
| (14.b) | n-C$_4$H$_9$ | 612 | 76 | 198 | 20 | 1.5 | 2.0 | 0.7 | +80 | +87 | +88 |
| (15.b) | n-C$_{10}$H$_{21}$ | 696 | 72 | >1440 | 287 | 113 | 24.8 | 4.6 | n.s. | n.s. | n.s. |
| (8.b) |  —(CH$_2$)$_2$—N⟨pyrrolidine⟩ | 803 | 115 | 394 | 31 | 2.0 | 0.9 | 2.3 | +212 | >+149 | +129 |
| (9.b) |  —(CH$_2$)$_x$—N⟨piperidine⟩ | 817 | 60 | 148 | 31 | 1.4 | 2.3 | 0.7 | +151 | +52 | +95 |
| 10 |  —(CH$_2$)$_2$—N⟨morpholine⟩ | 555 | 45 | 470 | 22 | 2.1 | 0.2 | 12.9 | +67 | +69 | +43 |

TABLE-continued

| Example | Active Ingredient R | LD$_{50}$ i.p. μmol/kg NW | LD$_{50}$ p.o. μmol/kg | Min. Symptom-dose μmol/kg | Isolated CF μmol/l | Guinea Pig FRP μmol/l | Atria CF/FRP | Aconitin-Rat ES Δ% | VT Δ% | KF Δ% |
|---|---|---|---|---|---|---|---|---|---|---|
| (19.b) | —(CH$_2$)$_3$—N(C$_2$H$_5$)$_2$ | 819 | 122 | 686 | 31 | 2.0 | 4.4 | 0.5 | +220 | +180 | +158 |
| (16.b) | —CH$_2$— | 646 | 483 | 2277 | (*) | 16.6 | 2.7 | 6.1 | +36 | +30 | +31 |
| 21 | —CH$_2$—CHOH— | 676 | 250 | 2175 | — | 3.2 | 3.8 | 0.8 | +89 | +92 | +72 |
| 22 | —CH$_2$—CHOH—CH$_2$—N | 697 | 168 | 550 | 72 | 3.4 | 8.1 | 0.4 | +154 | +121 | +110 |

Explanation:
n.s. = not significant
(*) = symptoms already indicating toxic area
— = not determined The following examples further illustrate the present invention yet without limiting the scope thereof.

The starting materials 10-bromoajmaline and 10-bromoisoajmaline are obtainable as described by Anet et al (Anet, Chakravarti, Robinson and Schlittler, J. Chem. Soc. 1954, Part I, p. 1242). The quaternary salts which are prepared from these starting materials according to the following examples are converted into the free aldehyde base which subsequently is reacted with L(+)-tartaric acid into the corresponding hydrogen tartrate. Aldehyde bases wherein the N-substituent is an alkyl group containing no additional nitrogen are reacted with an equimolar amount of tartaric acid. Aldehyde bases wherein the N-substituent is a nitrogen-containing group are reacted with twice the molar amount of tartaric acid (with the exception of Examples 10 and 22 where an equimolar amount of acid is used).

I. General procedure for obtaining the free aldehyde base.

The quaternary salt (about 10 g) is dissolved in 200 to 300 ml of water, the solution is rendered alkaline under cooling with ice and is extracted about five times with ethyl acetate (see the following variants A, B and D) or diethylether (see the following variant C).

II. General procedure for the preparation of the hydrogen tartrates.

Variant A:

The dried solution of the aldehyde base in ethyl acetate is evaporated, the residue is dissolved in a small amount of methanol, the calculated amount of L(+)-tartaric acid is added and the mixture is introduced dropwise into about 1 liter of ethyl acetate. The precipitated hydrogen tartrate is filtered off.

Variant B:

The dried solution of the aldehyde base in ethyl acetate is evaporated to a volume of about 100 ml, is filtered through cotton and is introduced dropwise into a solution of the calculated amount of L(+)-tartaric acid in 100 ml of acetone. The precipitated hydrogen tartrate is filtered off.

Variant C:

The solution of the extracted aldehyde base in diethylether is dried and evaporated. The residue is dissolved in as small as possible an amount of acetone and the resulting solution is introduced dropwise into a solution of the calculated amount of L(+)-tartaric acid in acetone. The precipitated hydrogen tartrate is filtered off.

Variant D:

The dried solution of the aldehyde base in ethyl acetate is evaporated to a volume of about 100 ml, is filtered through cotton and is introduced dropwise into a solution of the calculated amount of L(+)-tartaric acid which had been prepared by diluting a hot saturated solution of tartaric acid in acetone with one liter of ethyl acetate. The precipitated hydrogen tartrate is filtered off.

In case that the hydrogen tartrate is formed in amorphous form, the aldehyde base is once more liberated and the hydrogen tartrate is again precipitated as described above.

All yields which are given in the examples are calculated relative to the starting amount of bromoajmaline or bromoisoajmaline.

EXAMPLES 1 TO 14—ALKYLATION OF 10-BROMOAJMALINE

Example 1a

N$_b$-methyl-10-bromoajmalinium iodide.

10 g of 10-bromoajmaline and 8 ml of methyl iodide are dissolved in 350 ml of acetonitrile and the solution is heated under reflux for 8 hours. N$_b$-methyl-10-bromoajmalinium iodide crystallizes from the cooled solution.

Yield: 9.5 g (70%).

Melting point: 235° to 238° C., pure n-form.

Example 1b

N$_b$-methyl-10-bromoajmalinium hydrogen tartrate.

The hydrogen tartrate is prepared according to variant A.

Yield: 62%.

Melting point: 150° to 155° C., pure n-form.

Examples 2 to 6

The quaternary salts are prepared in a manner analogous to the method of Example 1 by reacting 10-bromoajmaline with 1-iodopropane (Example 2) or 1-iodohexane (Example 3) or allybromide (Example 4) or 1-iodo-3-methylbutane (Example 5) or 1-bromodecane (Example 6).

2a. $N_b$-propyl-10-bromoajmalinium iodide.
Yield: 93%.
Melting point: 273° C. (decomposing).
n-form:iso-form = about 3:1.

2b. $N_b$-propyl-10-bromoajmalinium hydrogen tartrate.
The hydrogen tartrate is prepared according to variant B.
Yield: 59%.
Melting point: 180° to 185° C.
n-form:iso-form = about 4:1.

3a. $N_b$-hexyl-10-bromoisoajmalinium iodide.
Yield: 53%.
Melting point: 220° to 223° C.
n-form:iso-form = about 1:4.

3b. $N_b$-hexyl-10-bromoisoajmalinium hydrogen tartrate.
The hydrogen tartrate is prepared according to variant B.
Yield: 45%.
Melting point: 160° to 165° C.
n-form:iso-form = about 2:3.

4a. $N_b$-allyl-10-bromoajmalinium bromide.
Yield: 80%.
Melting point: 245° to 248° C., pure n-form.

4b. $N_b$-allyl-10-bromoajmalinium hydrogen tartrate.
The hydrogen tartrate is prepared according to variant A.
Yield: 41%.
Melting point: 147° to 149° C., pure n-form.

5. $N_b$-(3-methylbutyl)-10-bromoajmalinium iodide.
The procedure of Example 1 is modified by carrying out the heating under reflux for 14 hours.
Yield: 65%.
Melting point: 240° to 245° C.
n-form:iso-form = about 2:1.

6a. $N_b$-decyl-10-bromoajmalinium bromide.
The procedure of Example 1 is modified by carrying out the heating under reflux for 12 hours.
Yield: 34%.
Melting point: 232° C.
n-form:iso-form = about 7:3.

6b. $N_b$-decyl-10-bromoajmalinium hydrogen tartrate.
The hydrogen tartrate is prepared according to variant B.
Yield: 21%.
Melting point: 112° to 115° C.
n-form:iso-form = about 1:1.

Example 7

7a. $N_b$-diethylaminoethyl-10-bromoisoajmalinium chloride.

10 g of 10-bromoajmaline are mixed with 5.72 g of 2-diethylaminoethyl chloride in 160 ml of absolute dioxane and the mixture is heated under reflux for a period of 9 hours. After cooling the product crystallizes and is filtered off under suction.
Yield: 9.6 g (72%).
Melting point: 211° to 213° C.

7b. $N_b$-diethylaminoethyl-10-bromoisoajmalinium bishydrogen tartrate.
The bishydrogen tartrate is prepared according to variant C.
Yield: 52%.
Melting point: 115° to 118° C.
n-form:iso-form = about 1:4.

Examples 8 to 10

The quaternary salts are prepared in a procedure analogous to Example 7 by reacting 10-bromoajmaline with 1-chloro-2-(1-pyrrolidinyl)ethane (Example 8) or 1-chloro-2-(1-piperidinyl)ethane (Example 9) or 1-chloro-2-(4-morpholinyl)ethane (Example 10). The hydrogen tartrates are prepared as in Example 7 according to variant C.

8a. $N_b$-(2-(1-pyrrolidinyl)ethyl)-10-bromoisoajmalinium chloride.
Yield: 48%.
Melting point: 233° to 235° C.

8b. $N_b$-(2-(1-pyrrolidinyl)ethyl)-10-bromoisoajmalinium bishydrogen tartrate.
Yield: 31%.
Melting point: 121° to 125° C.
n-form:iso-form = about 1:6.

9a. $N_b$-(2-(1-piperidinyl)ethyl)-10-bromoisoajmalinium chloride.
Yield: 64%.
Melting point: 234° to 236° C.

9b. $N_b$-(2-(1-piperidinyl)ethyl)-10-bromoisoajmalinium bishydrogen tartrate.
Yield: 39%.
Melting point: 124° to 127° C.
n-form:iso-form = about 1:2.

10a. $N_b$-(2-(4-morpholinyl)ethyl)-10-bromoajmalinium chloride.
The procedure of Example 7 is modified by carrying out the heating under reflux for 48 hours.
Yield: 53%.
Melting point: 225° to 229° C.

10b. $N_b$-[2-(4-morpholinyl)ethyl]-10-bromoisoajmalinium-chloride.

5 g 10-bromoajmaline and 2.4 g 2-(4-morpholinylethyl)-chloride are dissolved in 120 ml ethanol and heated for 48 hours under reflux. After concentration of the solution to about 40 ml and mixing with ether the product crystallizes out and is filtered off. Yield: 5.6 g (82%), Melting point 245° C. (decomposing), pure iso-form.

Examples 11 to 15

Alkylation of 10-bromoisoajmaline.

The quaternary salts are prepared according to a procedure analogous to Example 1 by reacting 10-bromoisoajmaline with methyl iodide (Example 11) or ethyl iodide (Example 12) or 1-iodopropane (Example 13) or 1-iodobutane (Example 14) or 1-bromodecane (Example 15). The hydrogen tartrates are prepared according to variant D.

11a. $N_b$-methyl-10-bromoisoajmalinium iodide.
Yield: 76%.
Melting point: 242° to 245° C., pure iso-form.

11b. $N_b$-methyl-10-bromoisoajmalinium hydrogen tartrate.
Yield: 57%.
Melting point: 128° to 132° C., pure iso-form.

12a. $N_b$-ethyl-10-bromo-isoajmalinium iodide.
Yield: 85%.

Melting point: 277° to 280° C., pure iso-form.

12b. $N_b$-ethyl-10-bromo-isoajmalinium hydrogen tartrate.

Yield: 72%.

Melting point: 110° to 130° C., pure iso-form.

13a. $N_b$-propyl-10-bromoisoajmalinium iodide.

Yield: 86%.

Melting point: 275° C. (decomposing).

n-form:iso-form = about 1:6.

13b. $N_b$-propyl-10-bromoisoajmalinium hydrogen tartrate.

Yield: 71%.

Melting point: 100° to 120° C.

n-form:iso-form = about 1:6.

14a. $N_b$-butyl-10-bromoisoajmalinium iodide.

Yield: 83%.

Melting point: 265° C. (decomposing).

n-form:iso-form = about 1:19.

14b. $N_b$-butyl-10-bromoisoajmalinium hydrogen tartrate.

Yield: 53%.

Melting point: 125° to 130° C.

n-form:iso-form = about 1:10.

15a. $N_b$-decyl-10-bromoisoajmalinium bromide.

Yield: 55%.

Melting point: 232° C.

n-form:iso-form = about 1:3.

15b. $N_b$-decyl-10-bromoisoajmalinium hydrogen tartrate.

Yield: 35%.

Melting point: 110° to 115° C.

n-form:iso-form = about 1:4.

Example 16

16a. $N_b$-benzyl-10-bromoisoajmalinium bromide.

A mixture of 10 g of 10-bromoisoajmaline 10 ml of benzylbromide and 40 ml of chloroform is agitated at room temperature for 24 hours. A small portion of the chloroform is evaporated under vacuum at room temperature and subsequently the product is crystallized by adding acetone and ether and cooling in a freezer compartment. The resulting crystals are recrystallized from methanol/ether.

Yield: 6 g (42%).

Melting point: 225° to 227° C., pure iso-form.

16b. $N_b$-benzyl-10-bromoisoajmalinium hydrogen tartrate.

The hydrogen tartrate is prepared according to variant D.

Yield: 25%.

Melting point: 130° to 132° C.

n-form:iso-form = about 1:5.

Example 17

$N_b$-(4-fluorobenzyl)-10-bromoisoajmalinium bromide.

10 g of 10-bromoisoajmaline and 10 ml of 4-fluorobenzyl bromide are dissolved in 100 ml of sulfolane (commercial name for 2,3,4,5-tetrahydrothiophane-1,1-dioxide) and are agitated for 1 hour at a temperature of 80° C. under nitrogen. Upon dilution with 200 ml of acetone the product precipitates. The precipitate is filtered off, washed with acetone and recrystallized from methanol/ether.

Yield: 12.8 g (73%).

Melting point: 247° C., pure iso-form.

Example 18

$N_b$-(4-methoxybenzyl)-10-bromoisoajmalinium chloride.

11 g of 10-bromoisoajmaline and 12 ml of 4-methoxybenzyl chloride are dissolved in 100 ml of sulfolane and the solution is agitated under nitrogen at a temperature of 80° C. for a period of 10 hours. The precipitated product is washed with acetone and is recrystallized from methanol/ethyl acetate.

Yield: 3.4 g (22%).

Melting point: 228° to 232° C., pure iso-form.

Example 19

19a. $N_b$-diethylaminopropyl-10-bromoisoajmalinium chloride.

The compound is prepared by reacting 10-bromoisoajmaline with diethylaminopropyl chloride in a procedure analogous to that of Example 7.

Melting point: 156° C.

n-form:iso-form = about 1:1.

19b. $N_b$-diethylaminopropyl-10-bromoisoajmalinium bishydrogen tartrate.

A small amount of water is added to the chloride precipitate which is obtained in Example 19a and which is still moistened with dioxane. The aqueous mixture is extracted with 100 ml of ether in order to remove excess alkylating agent. Subsequently the aldehyde base is liberated and the bishydrogen tartrate is prepared therefrom according to variant D.

Yield: 50%.

Melting point: 118° to 120° C.

n-form:iso-form = about 1:3.

Example 20

$N_b$-(2-hydroxyethyl)-10-bromoisoajmalinium chloride.

15 g of 10-bromoisoajmaline and 50 ml of chloroethanol are dissolved in 100 ml of sulfolane and the solution is agitated under nitrogen at a temperature of 80° C. for a period of 16 hours. Upon diluting with 1.5 liters of acetone the product precipitates. The precipitate is filtered off, washed with acetone and recrystallized from methanol/acetone.

Yield: 5.9 g (33%).

Melting point: 245° C., pure iso-form.

Example 21

$N_b$-(2-hydroxy-2-phenylethyl)-10-bromoisoajmalinium hydrogen tartrate.

10 g of bromoisoajmaline and 3.3 ml of epoxy styrene in 75 ml of ethanol are agitated at a temperature of 75° C. for a period of 7 hours. Then an additional 1 ml of epoxy styrene is added and the mixture is agitated for another 13 hours at 75° C. The reaction mixture is evaporated to dryness under vacuum, the residue is dissolved in methanol, a solution of 3.7 g of L(+)-tartaric acid in a small amount of methanol is added and the hydrogen tartrate is precipitated by introducing the reaction mixture dropwise into 1 liter of ethyl acetate.

Yield: 10.1 g (61%).

Melting point: 148° to 152° C.

Example 22

$N_b$-(2-hydroxy-3-(1-piperidinyl)propyl)-10-bromoisoajmalinium hydrogen tartrate.

10 g of bromoisoajmaline and 3.7 g of 3-piperidinopropylene oxide in 75 ml of ethanol are agitated at a temperature of 75° C. for a period of 8 hours. An additional 1 g of 3-piperidinopropylene oxide is added and the mixture is agitated for another 8 hours at 75° C. Then the solvent is distilled off under vacuum. The residue is dissolved in acetone and the solution is introduced dropwise into a solution of 3.9 g of L(+)-tartaric acid in 250 ml of acetone. The precipitated hydrogen tartrate is filtered off under suction. The aldehyde base is again liberated and is again reacted with 2.34 g of L(+)-tartaric acid to precipitate the hydrogen tartrate.
Yield: 10 g (58%).
Melting point: 130° to 135° C.
n-form:iso-form=about 2:3.

Example 23

23a. $N_b$-n-butyl-10-bromoajmalinium iodide.

10 g of bromoajmaline are dissolved in 250 ml of acetonitrile, 8 ml of 1-iodobutane are added and the reaction mixture is heated under reflux for 8 hours. The formed precipitate is filtered off and washed with methylene chloride.
Yield: 12.5 g (86%).
Melting point: 267° to 268° C.
n-form:iso-form=about 9:1.

23b. $N_b$-n-butyl-10-bromoajmalinium hydrogen tartrate.

Cold sodium carbonate solution is added to 11.8 g of $N_b$-n-butyl-10-bromoajmalinium iodide and the reaction mixture is exhaustingly extracted with ethyl acetate. The dried ethyl acetate solution is evaporated, methanol is added to the residue. Subsequently 3 g of L(+)-tartaric acid is added and a small portion of the reaction mixture is evaporated. The precipitated hydrogen tartrate is filtered off.
Yield: 9.3 g (76%).
Melting point: 151° C.
n-form:iso-form=about 9:1.

Example 24

$N_b$-(cyclopropylmethyl)-10-bromoajmalinium chloride.

12 g of bromoisojmaline and 10 g of chloromethylcyclopropane in 100 ml of sulfolane are heated to a temperature of 100° C. under nitrogen for a period of 36 hours. After cooling 400 ml of acetone are added to the reaction mixture and the precipitated crystals are filtered off. The crystals can be recrystallized from methanol.
Yield: 7.5 g (51%).
Melting point: 268° to 273° C.
n-form:iso-form=about 1:1.

Example 25

25a. $N_b$-(2-phenylethyl)-10-bromoisoajmalinium bromide.

8.5 g of 10-bromoajmaline are suspended in 50 ml of methanol, 3.2 ml of phenylethyl bromide are added and the reaction mixture is heated under reflux for 44 hours. The precipitated $N_b$-(2-phenylethyl)-10-bromoisoajmalinium bromide is filtered off and can be recrystallized from ethanol for further purification.
Yield: 8.1 g (65%).
Melting point: 210° to 212° C., iso-form.

25b. $N_b$-(2-phenylethyl)-10-bromoisoajmalinium hydrogen tartrate.

The hydrogen tartrate is prepared according to variant B.
Yield: 98%.

Melting point: 155° to 160° C., iso-form.

Example 26

Tablets containing $N_b$-propyl-10-bromoisoajmalinium hydrogen tartrate as active ingredient.

| Composition: | |
|---|---|
| Active ingredient | 15 parts |
| Lactose | 30 parts |
| Corn starch | 55 parts |
| Gelatin | 1 part |
| Aerosil 200* | 2 parts |
| Hydrogenated Castor Oil | 2 parts |
| Total | 105 parts |

Preparation:

The active ingredient is mixed with lactose and corn starch. The resulting mixture is moistened with an aqueous 15% solution of gelatin and is granulated. The moist material is passed through a 1.6 mm mesh size sieve, is dried on shelves at a temperature of 35° C. and subsequently is passed through a 1.0 mm mesh size sieve. After mixing the granulate with the dispersed silicium dioxide (Aerosil 200) and the powdered hydrogenated Castor Oil are pressed into tablets of 105 mg so that each tablet contains 15 mg of the active ingredient.

Example 27

Capsules containing $N_b$-propyl-10-bromoisoajmalinium hydrogen tartrate as active ingredient.

| Composition: | |
|---|---|
| Active ingredient | 15 parts |
| Lactose | 55 parts |
| Corn starch | 50 parts |
| Soluble starch | 3 parts |
| Aerosil 200 | 2 parts |
| Hydrogenated Castor Oil | 2 parts |
| Total | 127 parts |

Preparation:

The active ingredient is mixed with lactose and corn starch. The resulting mixture is moistened with an aqueous 15% solution of the soluble starch and is granulated. The moist material is passed through a 1.6 mm mesh size sieve, is dried on shelves at a temperature of 35° C. and subsequently is passed through a 1.0 mm mesh size sieve. After mixing the granulate with the dispersed silicium dioxide (Aerosil 200) and the powderized hydrogenated Castor Oil portions of 127 mg each of the mixture are automatically filled into hard gelatin capsules of size no. 4 so that each capsule contains 15 mg of the active ingredient.

Example 28

Tablets containing $N_b$-(2-(4-morpholinyl)ethyl)-10-bromoisoajmalinium chloride as active ingredient.

| Composition: | |
|---|---|
| Active ingredient | 15 parts |
| Lactose | 60 parts |
| Methyl cellulose 2000 cp | 10 parts |
| Corn starch | 15 parts |
| Aerosil 200 | 0.5 parts |
| Magnesium stearate | 0.5 parts |

-continued

| Composition: | |
|---|---|
| Total | 101 parts |

Preparation:

The active ingredient is first mixed with lactose, methyl cellulose and corn starch and subsequently the powderous dispersed silicium dioxide and the magnesium stearate which previously has been passed through a sieve of 0.2 mm mesh size are added. After thorough mixing of all ingredients the mixture is pressed in a rotating tabletting machine into tablets having a weight of 101 mg so that each tablet contains 15 mg of the active ingredient.

Example 29

Capsule containing $N_b$-[2-(4-morpholinyl)ethyl]-10-bromoisoajmalinium chloride as active ingredient.

| Composition: | |
|---|---|
| Active ingredient | 15 parts |
| Lactose D20 | 70 parts |
| Microcrystalline cellulose | 30 parts |
| Magnesium stearate | 1 part |
| Total | 116 parts |

Preparation:

The active ingredient is slowly mixed with lactose, microcrystalline cellulose and magnesium stearate. The powderous mixture is automatically filled in hard gelatin capsules of size no. 4 so that each capsule contains 15 mg of the active ingredient.

What is claimed is:

1. A $N_b$-quaternary 10-bromoajmaline and 10-bromoisoajmaline compound of the formula I wherein R is a carbon-attached organic residue containing 1 to 10 carbon atoms and having the formula II wherein n is 0 or 1; m is 0 or 1; x is hydrogen, hydroxy straight or branched alkyl which is unsubstituted or is substituted by hydroxy, alkoxy, halogen or dialkylamine, phenyl which is unsubstituted or is substituted by alkyl alkoxy or halogen, dialkylamine, pyrrolidine, piperidine or morpholine; and y is hydrogen, hydroxy or methyl or x and y together form a bond with the proviso that when y is hydroxy n is 1 and that when x and y together form a bond n and m each are 1 and $A^\ominus$ is an anion of a pharmacologically acceptable organic or inorganic acid.

2. The compound as defined in claim 1 wherein R is methyl, ethyl, allyl, propyl, butyl, 3-methylbutyl, hexyl, decyl, benzyl, 4-fluorobenzyl, 4-methoxybenzyl, 2-hydroxyethyl, 2-hydroxyl-2-phenylethyl, 2-diethylaminoethyl, 3-diethylaminopropyl, 2-(1-pyrrolidinyl)ethyl, 2-(1-piperidinyl)ethyl, 2-(4-morpholinyl)ethyl or 2-hydroxy-3-(1-piperidinyl)propyl.

3. The compound as defined in claim 1 wherein $A^\ominus$ is an anion of tartaric acid, oxalic acid, citric acid, hydrochloric acid or phosphoric acid.

4. The compound as defined in claim 3 wherein $A^\ominus$ is an anion of tartaric acid.

5. A compound of formula IV wherein R is a carbon-attached organic residue containing 1 to 10 carbon atoms and having the formula II wherein n is 0 or 1; m is 0 or 1; x is hydrogen, hydroxy, straight or branched alkyl which is unsubstituted or is substituted by hydroxy, alkoxy, halogen or dialkylamine, phenyl which is unsubstituted or is substituted by alkyl, alkoxy or halogen, dialkylamino, pyrrolidino, piperidino or morpholino; and y is hydrogen, hydroxy or methyl or x and y together form a bond with the proviso that when y is hydroxy n is 1 and that when x and y together form a bond, n and m each are 1.

6. The compound as defined in claim 5 wherein R is methyl, ethyl, allyl, propyl, butyl, 3-methylbutyl, hexyl, decyl, benzyl, 4-fluorobenzyl, 4-methoxybenzyl, 2-hydroxyethyl, 2-hydroxyl-2-phenylethyl, 2-diethylaminoethyl, 3-diethylaminopropyl, 2-(1-pyrrolidinyl)ethyl, 2-(1-piperidinyl)ethyl, 2-(4-morpholinyl)ethyl or 2-hydroxy-3-(1-piperidinyl)propyl.

7. A pharmaceutical composition comprising a cardiac rhythm regulative effective amount of a compound as defined in claim 1 and an inert pharmaceutical carrier.

8. A method of treating heart rhythm disorders in larger mammals which comprises administering to a larger mammal an effective amount of a compound as defined in claim 1.

* * * * *